US012285255B2

(12) United States Patent
Sheth et al.

(10) Patent No.: US 12,285,255 B2
(45) Date of Patent: Apr. 29, 2025

(54) SENSOR DEVICE-BASED DETECTION OF TRAUMA EVENTS AND RESPONSES

(71) Applicant: AT&T Intellectual Property I, L.P., Atlanta, GA (US)

(72) Inventors: Amee Sheth, Brick, NJ (US); Laura Nordyke, Kenmore, WA (US); Jay Shah, Monroe, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 349 days.

(21) Appl. No.: 17/677,083

(22) Filed: Feb. 22, 2022

(65) Prior Publication Data
US 2023/0263441 A1 Aug. 24, 2023

(51) Int. Cl.
*A61B 5/16* (2006.01)
*A61B 5/00* (2006.01)
*G06N 20/20* (2019.01)
*G16Y 40/10* (2020.01)

(52) U.S. Cl.
CPC ............ *A61B 5/165* (2013.01); *A61B 5/7465* (2013.01); *A61B 5/7475* (2013.01); *G06N 20/20* (2019.01); *G16Y 40/10* (2020.01)

(58) Field of Classification Search
CPC ..... A61B 5/165; A61B 5/7465; A61B 5/7475; A61B 5/0022; A61B 5/0077; A61B 5/1128; A61B 5/7267; G06N 20/20; G06N 20/00; G16Y 40/10
See application file for complete search history.

(56) References Cited

U.S. PATENT DOCUMENTS

| 11,228,810 B1* | 1/2022 | Arazi | H04N 21/251 |
| 2019/0197861 A1* | 6/2019 | Tunnell | A61B 5/0205 |
| 2020/0380404 A1* | 12/2020 | Rakshit | G16H 40/20 |
| 2023/0099519 A1* | 3/2023 | Beltran | G16H 50/20 |
| | | | 600/300 |

FOREIGN PATENT DOCUMENTS

| WO | WO-2021077142 A2 * | 4/2021 | H04L 67/303 |
| WO | WO-2022212052 A1 * | 10/2022 | A61B 5/024 |

OTHER PUBLICATIONS

Can, Y.S., et al., "Continuous Stress Detection Using Wearable Sensors in Real Life: Algorithmic Programming Contest Case Study", Sensors, Apr. 18, 2019, 21 pages, downloaded from https://www.ncbi.nlm.nih.gov/pmc/articles/PMC6515276/pdf/sensors-19-01849.pdf.

(Continued)

*Primary Examiner* — Quan Zhen Wang
*Assistant Examiner* — Rajsheed O Black-Childress

(57) ABSTRACT

A processing system including at least one processor may obtain data associated with a user, the data associated with the user including at least one of: visual data captured via at least one camera associated with the user or audio data captured via at least one microphone associated with the user, detect at least one trauma event of at least one defined trauma event type in at least one of the visual data or the audio data via at least one classification model, determine, responsive to detecting the at least one trauma event, a stress score based upon at least a portion of the data associated with the user in accordance with a stress prediction model, and generate an alert in response to the stress score exceeding a threshold.

20 Claims, 4 Drawing Sheets

(56) References Cited

OTHER PUBLICATIONS

Walambe, R., et al., "Employing Multimodal Machine Learning for Stress Detection", National Library of Medicine, Oct. 2021, downloaded from https://pubmed.ncbi.nlm.nih.gov/34745514/, 12 pages, DOI:10.1155/2021/9356452.
Ziliani, F., et al, "Performance Evaluation of Event Detection Solutions: the CREDS experience", Mitsubishi Electric Research Laboratories, TR2006-018, Sep. 2005, 8 pages, downloaded from https://citeseer.ist.psu.edu/viewdoc/summary;jsessionid=7149386674B3A9C8E89354F9CD01B842?doi=10.1.1.640.2859.

* cited by examiner

SENSOR DEVICE-BASED DETECTION OF TRAUMA EVENTS AND RESPONSES

The present disclosure relates generally to network-connected sensor devices, and more particularly to methods, computer-readable media, and apparatuses for determining a stress score in response to detecting a trauma event of a defined trauma event type in at least one of visual data or audio data via at least one classification model.

BACKGROUND

Current trends in wireless technology are leading towards a future where virtually any object can be network enabled and Internet Protocol (IP) addressable. The pervasive presence of wireless networks, including cellular, Wi-Fi, ZigBee, satellite and Bluetooth networks, and the migration to a 128-bit IPv6-based address space provides the tools and resources for the paradigm of the Internet of Things (IoT) to become a reality. In addition, the household use of various sensor devices is increasingly prevalent. These sensor devices may relate to biometric data, environmental data, premises monitoring, and so on.

SUMMARY

In one example, the present disclosure describes a method, computer-readable medium, and apparatus for determining a stress score in response to detecting a trauma event of a defined trauma event type in at least one of visual data or audio data via at least one classification model. For example, a processing system including at least one processor may obtain data associated with a user, the data associated with the user including at least one of: visual data captured via at least one camera associated with the user or audio data captured via at least one microphone associated with the user, detect at least one trauma event of at least one defined trauma event type in at least one of the visual data or the audio data via at least one classification model, determine, responsive to detecting the at least one trauma event, a stress score based upon at least a portion of the data associated with the user in accordance with a stress prediction model, and generate an alert in response to the stress score exceeding a threshold.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
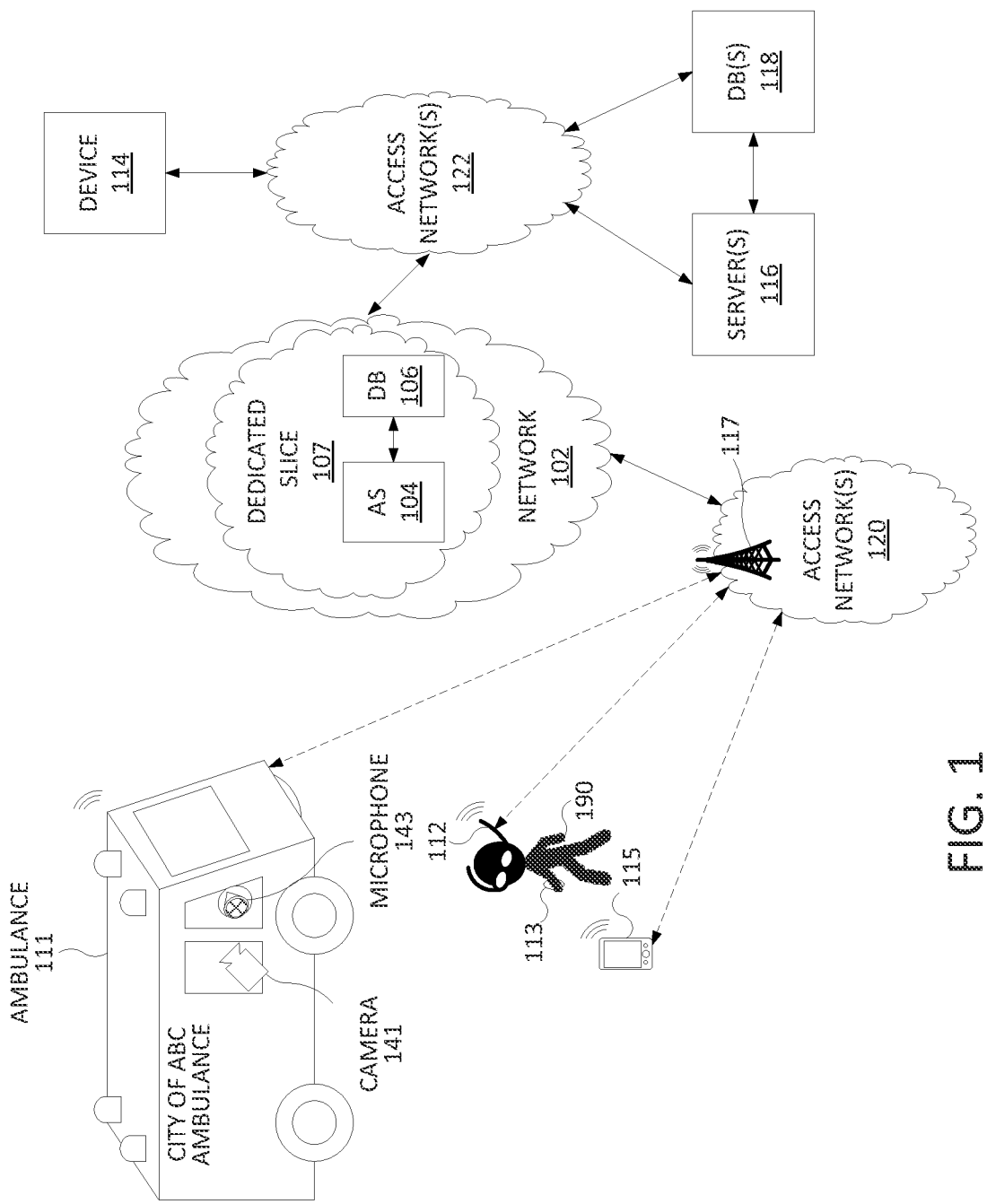
FIG. 1 illustrates an example network related to the present disclosure.

Examples of the present disclosure provide for methods, computer-readable media, and apparatuses for determining a stress score in response to detecting a trauma event of a defined trauma event type in at least one of visual data or audio data via at least one classification model. In particular, examples of the present disclosure provide an attribute-based temporal analysis through the correlation of various factors associated with trauma events to detect and prevent negative repercussions. Examples of the present disclosure are described herein illustratively in connection with personal computing devices and systems utilized by first responders (e.g., firefighters, police, emergency medical service (EMS) personnel, etc.). However, examples of the present disclosure may further apply in related contexts, such as for military personal computing devices and systems, or those of transportation professionals (e.g., truckers, delivery workers, taxi drivers, etc.) who may experience certain types of work related trauma events.

For instance, examples of the present disclosure may detect trauma events in visual and/or audio data collected from one or more cameras and/or one or more microphones associated with a user. The cameras or microphones may be body-worn devices, such as an outward facing camera mounted on a vest, a helmet-mounted camera, an outward facing camera of a user's glasses (e.g., smart glasses, or the like), and so forth. Alternatively, or in addition, the camera(s) and/or microphone(s) may be of a vehicle in which the user is an operator or passenger (e.g., an ambulance, police vehicle, fire truck or engine, etc.). Examples of the present disclosure may then detect one or more instances of trauma events of one or more defined trauma event types within the visual or audio data collected from such camera(s) and/or microphone(s). For instance, in accordance with the present disclosure, different types of professionals may have different sets of defined trauma events that may be scanned for and detected in the visual and/or audio data. For example, for EMS users, defined trauma events types may include any apparent human loss of life, loss of limb of a child, disfigurement, etc. For firefighters defined trauma events types may include some or all of the foregoing and may further include loss of life of domestic animals/pets, loss of life of livestock, loss of life of a fellow firefighter, or the like. Other defined trauma event types may include loss of oxygen, loss of consciousness, or other professionals or members of the public suffering the same and who are encountered by a given user, burned skin, loss of limb(s), significant blood loss, and so on. It should be noted that in one example, the defined trauma events may be less extensive and/or different for EMS users since a greater level of trauma is expected due to the nature of the work. However, in other examples, this may not be the case. For example, it may not be appropriate to assume that EMS users are more sensitized to traumatic events or, alternatively, desensitized to traumatic events. Rather, the trauma events may simply be detected and noted, and the user's response tracked via a stress score. Thus, trauma events may not negatively affect a user's stress score, or may only minimally impact the stress score. However, in the event that a user has a strong negative response following any one or more defined trauma events, such response may be detected and proactively addressed via devices and systems of the present disclosure. To further illustrate, for police users, defined trauma event types may include some or all of the foregoing, and additionally may include a discharge of firearm event (by the user or by one or more others in the vicinity of the user), assault and/or combat involving knives or the like, hand-to-hand combat, high-speed chase (or any vehicular or on-foot chase), and so forth. It should be noted that the foregoing are just several examples that are illustrative of the types of trauma events that may be detected in visual and/or audio data from camera(s) and/or microphone(s) associated with a user and that other, further, and/or different examples may be provided in various examples depending upon the nature of the type of professional for which monitoring is being provided, organizational preferences and/or requirements, and so forth.

In any case, defined trauma events may have associated classification models in accordance with the present disclosure, e.g., machine learning models (MLMs) or the like, for detecting semantic content in visual and/or audio data. For instance, the sematic content may comprise "gun fire," "drawn weapon," "foot chase," "vehicular chase," "hand-to-hand combat," "deceased pet," "missing limb," "human in severe pain," "animal in severe pain," and so forth. It should be noted that in some examples, the audio data may include defined spoken profession-specific terms, which may include code words, such as "code blue," "patient is coding," "triple zero," "B-I-D," "M-C-I," etc. In addition, the detection models may be trained or otherwise configured to detect these profession-specific (or organization-specific) terms or phrases.

In response to detecting an occurrence of one or more defined trauma events for a given user, the present disclosure may then determine a stress score for the user, and may continue to update and monitor the stress score to determine if the stress score exceeds a threshold (e.g., indicative that intervention may be warranted). The stress score may be determined in accordance with a stress prediction model, e.g., a MLM, a regression model, or a formula-based model. The stress prediction model may be trained to take a plurality of stressor indicators as inputs and to output a stress score (e.g., a numeric score on a scale of 0 to 100, negative 100 to positive 100, or the like, or a score on a binary scale, e.g., (1) excessive stress or (0) no excessive stress, or the like). The stressor indicators may be determined from various data points pertaining to a user from several sources. For instance, calendar data of the user may indicate a quantity of time at work for the user (e.g., within a given week, a rolling 7 day time period, etc.), at least one personal event of the user (such as attending a funeral, visiting a family member in hospice, or the like), and so forth. Similarly, location data of a user's personal mobile computing device may indicate a commute time of the user for the current day, a quantity of time commuting within the past week, or the like, an amount of screen time of the user on the device, stops at locations of significance, such as time at home, time at a casino, time at a bar, etc., an amount of time or money spent on certain applications (apps) on the device (e.g., spending unusual amounts on an online gambling app, making large in-game purchases for online video games, etc.), and so forth.

Other data may include biometric data of the user, e.g., the user's heart rate, breathing rate, sleep/wake times and/or patterns, or the like, environmental and/or weather data, such as the daily temperature, weekly average temperature, daily sunlight, and so forth. The biometric data may be obtained from a wearable sensor and/or wearable computing device of the user, such as a heart rate monitor, a smartwatch, a fitness band, and so forth (broadly a "biometric device"). Environmental data may be obtained from sensors of the user's mobile computing device, or in communication with the user mobile computing device, or may be obtained from one or more public databases based upon the location data of the user. The data may be from one or more defined time periods before, contemporaneous with, or after a detected trauma event. For instance, the last week, 30 days, or month of sleep/wake data may be used an input, or inputs. Alternatively, or in addition, data may continue to be collected and input to the stress prediction model over a period of time after a detected trauma event, e.g., the next 48 hours, the next week, the next two weeks, the next month, etc. For example, a user may have a delayed onset of stress or may initially handle a traumatic event well, but may have a significant number of additional stressors after the event that may overwhelm the user. Thus, an input data set associated with the user may continue to be updated with new data which may be input to the stress prediction model on a rolling basis (e.g., every six hours, daily, etc.). In one example, the input data set may be updated to remove old data. Alternatively, or in addition, data may be collected and stored for 30 days or other time periods, but may be aggregated with new data and may be stored and used for a longer period of time in response to a detected trauma event (or events). In one example, different types of data associated with a user may have different retention periods. For instance, weather data for the last two weeks may be considered relevant, but older data may have less significance, whereas sleep data for the last month may still be relevant and thus stored for a longer period of time.

The stress prediction model may be trained using a plurality of such data points as inputs/predictors, and may output a stress score as noted above. For instance, a training data set may comprise data sets/input vectors comprising sets of the above data points of users having quantified/known stress scores, e.g., users who have voluntarily sought help in the past, or who have been approached with offers of assistance and who have voluntarily participated and indicated a willingness for the above data points from a relevant time period to be used as training data for training and/or retraining the stress prediction model. In other words, the training data may comprise labeled samples (e.g., labeled with the known stress scores). Known stress scores may be determined for example by questionnaires/self-reporting, professional evaluation, or the like. The stress scores may be on a stress scale, e.g., a perceived stress scale (PSS). As such, the stress prediction model may learn and be trained to output/predict stress scores based upon input vectors of available data relating to a subject user.

In one example, user data may be stored locally on a computing device of the user and the stress prediction model may also be implemented locally by the user's computing device. In another example, user data may be uploaded and stored securely in one or more network-based data storage systems and may be accessed and utilized only upon the request of the user, or with the affirmative consent of the user. Similarly, in one example, the trauma event detection may be applied locally by the user's computing device. However, in another example, trauma event detection using traumatic event detection models associated with various defined trauma event types may be applied by a network-based processing system (e.g., public or private cloud-based servers, or the like, one or more servers of an first responder organization (e.g., a fire department computing system, an EMS unit computing system, etc.), and so forth). In one example, user's image and/or audio data is not stored any longer than necessary to determine if one or more trauma events is/are detected to be present or not. A detection of a traumatic event may be recorded and stored, and/or notified to one or more computing devices associated with the user (e.g., such as to the user's smartphone), while the image and/or audio data may then be deleted, overwritten, etc. immediately or as soon as practicable.

It should be noted that by nature of their responsibilities, first responders work in and are exposed to stressful environments. Examples of the present disclosure provide an interactive and predictive process that provides first responders or similar users with personalized recommendations or interventions based on various data relating to the users, their ecosystems, and peer users. For instance, an alert/warning may be provided to the user via the user's smartphone or other computing devices. In one example, such a warning/alert may alternatively or additionally be transmitted to an authorized person or entity, e.g., designated by the user. For example, the user may authorize a partner, spouse, parent, child, or other family member(s) to receive warnings/alerts. Similarly the user may authorize an employer (e.g., a police department, fire department, EMS unit, etc.) to receive such an alert/warning. In such case, there may be a designated individual or unit within the organization that is specifically designated and authorized to receive the warning/alert, where such information is not made available to the user's supervisor(s), direct co-workers, or any other individuals within the organization who do not have a need to know and/or who are not specifically authorized by the user. For instance, the user may have a prior relationship with a staff psychologist whom the user has specifically authorized to receive alerts/warnings, but any other individuals in the organization are not authorized and thus will not be alerted to anything related to the user. In one example, one or more automated interventions may also be applied. In addition, in one example, the automated intervention(s) may be pre-selected and/or pre-approved by the user. For example, an application of the present disclosure operating on the user's smartphone may be authorized to place limits on credit card usage, cash withdrawal, in-app purchases for other apps on the device, or the like, and so on. Alternatively, or in addition, the smartphone may place screen time limits on one or more apps or the device overall, and/or may place similar screen time limits on other devices associated with the user, such as limiting excessing television watching. It should be noted that such limits may not be strict limits, but may comprise pausing a program to present a reminder to the user and a suggestion to stop, logging a user out, etc. For instance, the user may choose to ignore such a subsequent reminder by logging back in, turning a device back on, etc. Thus, examples of the present disclosure provide gradations of responses that may be pre-approved by the user. As such, examples of the present disclosure operate with the user's consent and for the benefit of the user as an opt-in service. These and other aspects of the present disclosure are discussed in greater detail below in connection with the examples of FIGS. 1-4.

To further aid in understanding the present disclosure, FIG. 1 illustrates an example system 100 in which examples of the present disclosure may operate. The system 100 may include any one or more types of communication networks, such as a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, 4G, 5G and the like), a long term evolution (LTE) network, and the like, related to the current disclosure. It should be noted that an IP network is broadly defined as a network that uses Internet Protocol to exchange data packets. Additional example IP networks include Voice over IP (VoIP) networks, Service over IP (SoIP) networks, and the like.

In one example, the system 100 may comprise a network 102, e.g., a core network of a telecommunication network. The network 102 may be in communication with one or more access networks 120 and 122, and the Internet (not shown). In one example, network 102 may combine core network components of a cellular network with components of a triple play service network; where triple-play services include telephone services, Internet services and television services to subscribers. For example, network 102 may functionally comprise a fixed mobile convergence (FMC) network, e.g., an IP Multimedia Subsystem (IMS) network. In addition, network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Network 102 may further comprise a broadcast television network, e.g., a traditional cable provider network or an Internet Protocol Television (IPTV) network, as well as an Internet Service Provider (ISP) network. In one example network 102 may include a dedicated slice 107, e.g., a "network slice" that is reserved for first responders and/or governmental entities or quasi-governmental entities. For instance, dedicated slice 107 may comprise cellular core network components that service such entities, users associated with such entities, and/or their endpoint devices, while other users, entities, and/or their endpoint devices may be serviced by a different network slice, or slices. In one example, dedicated slice 107 may include an application server (AS) 104 and database (DB) 106, as discussed in further detail below. In one example, network 102 may also include a plurality of television (TV) servers (e.g., a broadcast server, a cable head-end), a plurality of content servers, an advertising server, an interactive TV/video-on-demand (VoD) server, and so forth. For ease of illustration, various additional elements of network 102 are omitted from FIG. 1.

In one example, the access networks 120 and 122 may comprise Digital Subscriber Line (DSL) networks, public switched telephone network (PSTN) access networks, broadband cable access networks, Local Area Networks (LANs), wireless access networks (e.g., an IEEE 802.11/Wi-Fi network and the like), cellular access networks, 3$^{rd}$ party networks, and the like. For example, the operator of network 102 may provide a cable television service, an IPTV service, or any other types of telecommunication service to subscribers via access networks 120 and 122. In one example, the access networks 120 and 122 may comprise different types of access networks, may comprise the same type of access network, or some access networks may be the same type of access network and other may be different types of access networks. In one example, the network 102 may be operated by a telecommunication network service provider. The network 102 and the access networks 120 and 122 may be operated by different service providers, the same service provider or a combination thereof, or may be operated by entities having core businesses that are not related to telecommunications services, e.g., corporate, governmental or educational institution LANs, and the like. In one example, each of access networks 120 and 122 may include at least one access point, such as a cellular base station, non-cellular wireless access point, a digital subscriber line access multiplexer (DSLAM), a cross-connect box, a serving area interface (SAI), a video-ready access device (VRAD), or the like, for communication with various endpoint devices. For instance, as illustrated in FIG. 1, access network(s) 120 include a wireless access point 117 (e.g., a cellular base station).

In one example, the access networks 120 may be in communication with various devices or computing systems/processing systems, such as mobile device 115, augmented reality (AR) device 112 (e.g., AR eyewear), biometric device 113, ambulance 111 (e.g., a computing device and/or processing system thereof), camera 141, microphone 143, and so forth. Similarly, access networks 122 may be in communication with one or more devices, e.g., device 114, server(s) 116, database(s) (DB(s)) 118, etc. Access networks 120 and 122 may transmit and receive communications between mobile device 115, AR device 112, biometric device 113, ambulance 111, camera 141, and/or microphone 143, and so forth, and server(s) 116 and/or DB(s) 118, application server (AS) 104 and/or database (DB) 106, other components of network 102, devices reachable via the Internet in general, and so forth.

In accordance with the present disclosure, a user, such as user 190, may be equipped with various devices, such as mobile device 115, AR device 112, and biometric device 113. For instance, mobile device 115 may comprise a cellular smart phone, a laptop, a tablet computer, or the like. AR device 112 may comprise a wearable computing device, e.g., smart glasses, or the like. Likewise biometric device 113 may comprise a wearable computing device, e.g., a smart watch, a fitness band, etc. In accordance with the present disclosure, mobile device 115, AR device 112, and/or biometric device 113 may each include one or more sensors for tracking location, speed, distance, altitude, or the like (e.g., a Global Positioning System (GPS) unit), for tracking orientation (e.g., gyroscope and compass), and so forth. Biometric device 113 may also include sensors for measuring, recording, and reporting temperature, heart rate, breathing rate, blood oxygen, and so forth. It should be noted that user 190 may alternatively or additionally be equipped with other devices, such as a chest-mounted camera ("bodycam"), which in one example may further include at least one microphone, a push-to-talk (PTT) radio unit, and so forth.

In accordance with the present disclosure, mobile device 115, AR device 112, and/or biometric device 113 may each include one or more radio frequency (RF) transceivers for cellular communications and/or for non-cellular wireless communications. Ambulance 111 may be similarly equipped with one or more radio frequency (RF) transceivers for cellular communications and/or for non-cellular wireless communications. In one example, camera 141 and microphone 143 may comprise network-connected "Internet of Things" (IoT) devices. Alternatively, or in addition, camera 141 and/or microphone 143 may transmit data to remote destination devices or systems via a processing system and radio communication unit(s) of ambulance 111. In one example, device 114 may comprise a mobile device, a cellular smart phone, a laptop, a tablet computer, a desktop computer, a wearable computing device (e.g., a smart watch, a smart pair of eyeglasses, etc.), an application server, a bank or cluster of such devices, or the like.

In one example, mobile device 115 may include an application (app) for traumatic stress monitoring, and which may establish communication with server(s) 116 to provide visual and/or audio data, to receive or provide other data associated with user 190, and so forth. For instance, as illustrated in FIG. 1, access networks 122 may be in communication with one or more servers 116 and one or more databases (DB(s)) 118. Alternatively, or in addition, mobile device 115 may have a web browser via which a traumatic stress monitoring website may be accessed. In accordance with the present disclosure, each of the server(s) 116 may comprise a computing system or server, such as computing system 400 depicted in FIG. 4, and may individually or collectively be configured to perform operations or functions for determining a stress score in response to detecting a trauma event of a defined trauma event type in at least one of visual data or audio data via at least one classification model (such as illustrated and described in connection with the example method 300 of FIG. 3). For instance, server(s) 116 may host a traumatic stress monitoring app or website via which users may request traumatic stress monitoring and via which such users may obtain notifications of undue stress in response to one or more detected traumatic events of one or more defined trauma event types.

Figure 4:
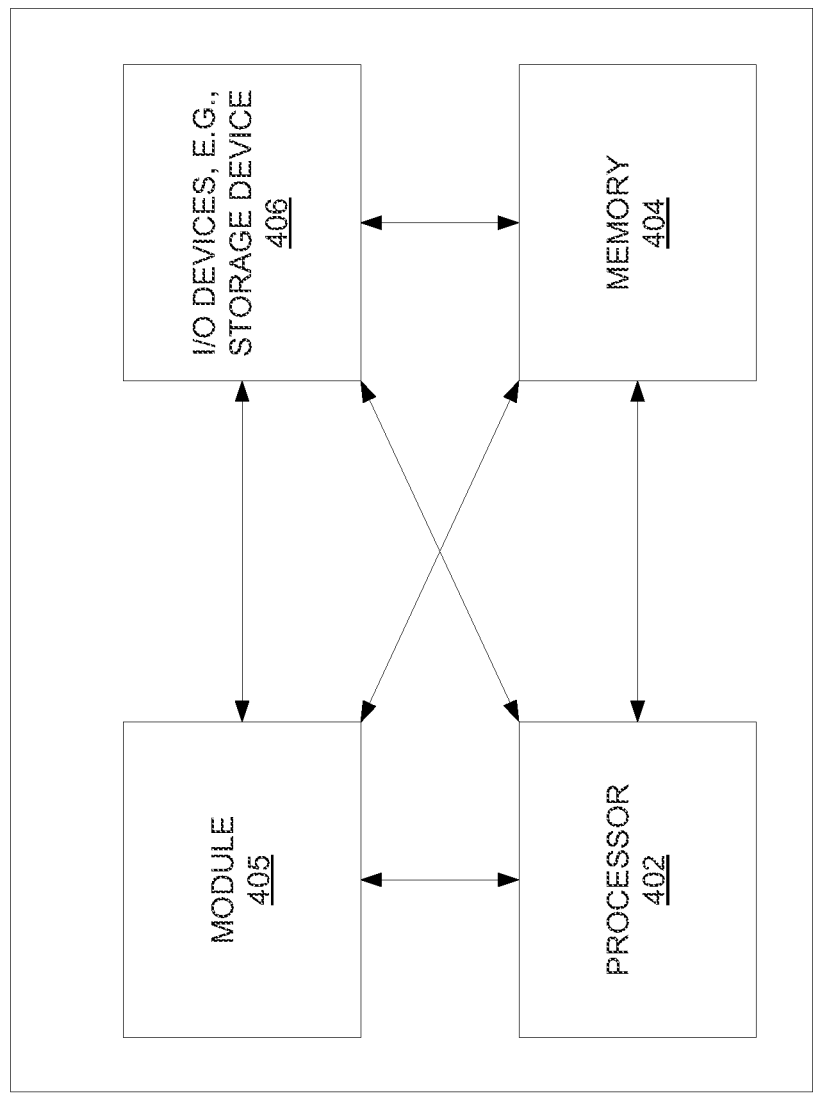
FIG. 4 illustrates a high level block diagram of a computing device specifically programmed to perform the steps, functions, blocks and/or operations described herein.

It should be noted that as used herein, the terms "configure," and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device including one or more processors, or cores (e.g., as illustrated in FIG. 4 and discussed below) or multiple computing devices collectively configured to perform various steps, functions, and/or operations in accordance with the present disclosure.

In one example, DB(s) 118 may comprise one or more physical storage devices integrated with server(s) 116 (e.g., a database server), attached or coupled to the server(s) 116, or remotely accessible to server(s) 116 to store various types of information in support of systems for determining a stress score in response to detecting a trauma event of a defined trauma event type in at least one of: visual data or audio data via at least one classification model, in accordance with the present disclosure. For example, DB(s) 118 may include a user database to store a record for each user that may include video and/or audio data collected from devices associated with each user. For instance, for user 190, a record in DB(s) 118 may include identifications of mobile device 115, AR device 112, and/or biometric device 113, video and/or audio data collected from any one or more of such devices, other sensor data collected from such devices, which may include weather data (e.g., temperature, humidity, etc.), biometric data (e.g., heart rate, breathing rate, sleep/wake data), and so forth. In addition, DB(s) 118 may comprise one or more geographic databases, e.g., storing maps and/or geographic data sets. For instance, DB(s) 118 may store a map/geographic data set for an area that may include landmarks that may be relevant to traumatic stress monitoring. In one example, DB(s) 118 may also store a database of detection models, e.g., machine learning models (MLMs) or the like, for detecting semantic content in video and/or audio data (e.g., traumatic events of defined trauma event types), and prediction models, e.g., for predicting stress scores based on sensor data associated with users, and so forth.

In an illustrative example, user 190 may register and authorize server(s) 116 to track aspects of the user's daily work and non-work activities, and sensor data associated with the user (e.g., biometric data) or the user's environment for purposes of traumatic stress monitoring, detection, and alerting. In one example, server(s) 116 may offer a service to users of selected organizations, such as first responders, transportation workers, or the like. In one example, user 190 may provide identification information regarding the user's devices, such as mobile device 115, AR device 112, and/or biometric device 113, and may authorize server(s) 116 to request and collect video, audio, and/or other sensor data from such devices. In addition, the user 190 may grant server(s) 116 authorization to access calendar data, device usage data (e.g., the amount of screen time, the applications used, an amount of in-app purchases, etc.), and so forth for any one or more of such devices.

In one example, server(s) 116 may collect and store in DB(s) 118 such data (broadly "user data") over one or more defined time periods (e.g., 90 days, 60 days, 30 days, 14 days, etc.). In one example, different types of user data may be stored over different time periods. Thus, DB(s) 118 may store user data of user 190 and others on a rolling basis. In addition, server(s) 116 may receive visual data and/or audio data from AR device 112, such as a video feed, which may further include or may be accompanied by an audio feed. Server(s) 116 may then scan the visual and/or audio data for any trauma events of one or more defined trauma event types.

In an illustrative example, server(s) 116 may apply detection, or classification models (e.g., MLMs or the like stored in DB(s) 118) for detecting semantic content in visual data (e.g., traumatic events, such as human loss of life, loss of limb of a child, disfigurement, burned skin, loss of limb(s), loss of life of domestic animals/pets, loss of life of livestock, etc.). In one example, server(s) 116 may train and/or deploy MLMs for a defined set of trauma event types, such as those noted above. In one example, different sets of defined trauma event types may be monitored for different categories of users and/or for different organizations to which the users may be associated (e.g., different sets for police, fire, EMT, etc.).

In the case of image or audio data, in one example DB(s) 118 may store and server(s) 116 may apply various semantic content detection/classification models, e.g., MLMs or other detection models, for identifying relevant semantic content/features (e.g., trauma events or other semantic content) within the image and/or audio data. For example, in order to detect semantic content of "discharged firearm" in image data, server(s) 116 may deploy a detection model (e.g., stored in DB(s) 118). This may include one or more images of discharging firearms (e.g., from different angles, in different scenarios, different types of firearms, etc.), and may alternatively or additionally include feature set(s) derived from one or more images and/or videos of discharging firearms, respectively. For instance, DB(s) 118 may store a respective scale-invariant feature transform (SIFT) model, or a similar reduced feature set derived from image(s) of discharging firearms, which may be used for detecting additional instances of discharging firearms in image data via feature matching. Thus, in one example, a feature matching detection algorithm/model stored in DB(s) 118 may be based upon SIFT features. However, in other examples, different feature matching detection models/algorithms may be used, such as a Speeded Up Robust Features (SURF)-based algorithm, a cosine-matrix distance-based detector, a Laplacian-based detector, a Hessian matrix-based detector, a fast Hessian detector, etc.

The visual features used for detection of "discharged firearm" or other semantic content (such as severe burns, hand-to-hand combat, deceased livestock, etc.) may include low-level invariant image data, such as colors (e.g., RGB (red-green-blue) or CYM (cyan-yellow-magenta) raw data (luminance values) from a CCD/photo-sensor array), shapes, color moments, color histograms, edge distribution histograms, etc. Visual features may also relate to movement in a video and may include changes within images and between images in a sequence (e.g., video frames or a sequence of still image shots), such as color histogram differences or a change in color distribution, edge change ratios, standard deviation of pixel intensities, contrast, average brightness, and the like.

In one example, server(s) 116 may perform an image salience detection process, e.g., applying an image salience model and then performing an image recognition algorithm over the "salient" portion of the image(s) or other image data/visual information, such as from camera 141, AR device 112, or the like. Thus, in one example, visual features may also include a length to width ratio of an object, a velocity of an object estimated from a sequence of images (e.g., video frames), and so forth. Similarly, in one example, server(s) 116 may apply an object/item detection and/or edge detection algorithm to identify possible unique items in image data (e.g., without particular knowledge of the type of item; for instance, the object/edge detection may identify an object in the shape of a person in a video frame, without understanding that the object/item is a person). In this case, visual features may also include the object/item shape, dimensions, and so forth. In such an example, object/item recognition may then proceed as described above (e.g., with respect to the "salient" portions of the image(s) and/or video(s)).

It should be noted that as referred to herein, a machine learning model (MLM) (or machine learning-based model) may comprise a machine learning algorithm (MLA) that has been "trained" or configured in accordance with input training data to perform a particular service, e.g., to detect a trauma event of a defined trauma event type or other semantic content. In one example, MLM-based detection models associated with image/visual data inputs may be trained using samples of video or still images that may be labeled by participants or by human observers with dispositions (and/or with other semantic content labels/tags). For instance, a machine learning algorithm (MLA), or machine learning model (MLM) trained via a MLA may be for detecting a single semantic concept, or may be for detecting a single semantic concept from a plurality of possible semantic concepts that may be detected via the MLA/MLM. For instance, the MLA (or the trained MLM) may comprise a deep learning neural network, or deep neural network (DNN), such as convolutional neural network (CNN), a generative adversarial network (GAN), a support vector machine (SVM), e.g., a binary, non-binary, or multi-class classifier, a linear or non-linear classifier, and so forth. In one example, the MLA may incorporate an exponential smoothing algorithm (such as double exponential smoothing, triple exponential smoothing, e.g., Holt-Winters smoothing, and so forth), reinforcement learning (e.g., using positive and negative examples after deployment as a MLM), and so forth. It should be noted that various other types of MLAs and/or MLMs, or other detection models may be implemented in examples of the present disclosure such as a gradient boosted decision tree (GBDT), k-means clustering and/or k-nearest neighbor (KNN) predictive models, support vector machine (SVM)-based classifiers, e.g., a binary classifier and/or a linear binary classifier, a multi-class classifier, a kernel-based SVM, etc., a distance-based classifier, e.g., a Euclidean distance-based classifier, or the like, a SIFT or SURF features-based detection model, as mentioned above, and so on. In one example, MLM-based detection models may be trained at a network-based processing system (e.g., server(s) 116) and deployed to sensor devices, such as camera 141, microphone 143, etc.). Similarly, non-MLM-based detection/classification models may be generated by server(s) 116, e.g., based upon feature sets from sample input data as described above. It should also be noted that various pre-processing or post-recognition/detection operations may also be applied. For example, server(s) 116 may apply an image salience algorithm, an edge detection algorithm, or the like (e.g., as described above) where the results of these algorithms may include additional, or pre-processed input data for the one or more detection models.

Similarly, server(s) 116 may generate, store (e.g., in DB(s) 118), and/or use various speech or other audio detection models, which may be trained from extracted audio features from one or more representative audio samples, such as low-level audio features, including: spectral centroid, spectral roll-off, signal energy, mel-frequency cepstrum coefficients (MFCCs), linear predictor coefficients (LPC), line spectral frequency (LSF) coefficients, loudness coefficients, sharpness of loudness coefficients, spread of loudness coefficients, octave band signal intensities, and so forth, wherein the output of the model in response to a given input set of audio features is a prediction of whether a particular semantic content is or is not present (e.g., sound indicative of a discharged firearm, the sound of breaking glass (or not), sounds of someone in severe pain or distress, specific words or phrases, which in accordance with the present disclosure may include profession-specific terms or codes, etc.). For instance, in one example, each audio model may comprise a feature vector representative of a particular sound, or a sequence of sounds.

Thus, server(s) 116 may obtain visual and/or audio data from one or more devices of user 190, and/or from vehicles or an environment associated with user 190 (such as camera 141 and/or microphone 143 of ambulance 111) and may detect one or more trauma events of one or more defined trauma event types in accordance with one or more classification/detection models such as described above. In accordance with the present disclosure, following the detection of one or more trauma events, server(s) 116 may then analyze additional data associated with user 190 to identify whether user 190 is predicted to be suffering from excessive stress (and/or whether it is predicted that user 190 will experience excessive stress at some point in the future (e.g., within a defined time period following the one or more traumatic events, such as within the next two week, the next 30 days, the next 60 days, etc.)). In addition, server(s) 116 may perform this analysis on an ongoing basis for a certain period of time, such as daily, twice daily, etc. for 30 days, 60 days, etc. following a defined trauma event.

In one example, server(s) 116 may train and run a stress prediction model. In one example, the stress prediction model may comprise a machine learning model trained on a plurality of sets of data associated with a plurality of users. The stress prediction model may comprise, for example, a DNN, such as a CNN, a GBDT, or other MLM such as described above. Alternatively, the stress prediction model may comprise a regression model or a formula-based model. In one example, different stress prediction models may be trained and deployed for different types of users (e.g., different categories of first responders, transportation professionals, etc.). In one example, each of the plurality of sets of data may be labeled with a respective stress score, or a respective label of excess stress or non-excess stress. The stress scores/labels may be self-reported by users, such as via questionnaires, or may be recorded by professionals from whom the users have sought assistance (and to whom the users have provided consent to use such data for stress prediction model training). The stress scores may be on a stress scale, e.g., a perceived stress scale (PSS). As such, the stress prediction model may learn and be trained to output/predict a stress scores based upon an input vector of available user data relating to user 190.

As noted above, user data may be stored in DB(s) 118 and may include calendar data of the user, location data of a user's personal mobile computing device (or devices), usage data of the device(s), biometric data of the user, environmental and/or weather data, and so on. Accordingly, in one example, server(s) 116 may retrieve and process such data from DB(s) 118. In one example, stressor indicators may be extracted from the user data, such as a quantity of time at work, at least one scheduled personal event of the user, a commute time of the user for the current day, a quantity of time commuting within the past week, or the like, stops at locations of significance (which may be determined by cross-referencing device location data with known locations from a database (e.g., locations of bars, casinos, etc.), an amount of time spent at home, an amount of screen time of the user on one or more computing devices, an amount of time or money spent on certain apps, and so forth. In one example, stressor indicators, or stressors, may be identified in biometric data of the user, such as excessive heart rate (e.g., average daily heart rate over a threshold percentage from a normal resting heart rate of the user and/or over a fixed threshold, which may be keyed to a user's age, gender, and/or other demographic characteristics), breath holding patterns detected, and so forth. Similarly, stressor indicators may be identified in environmental and/or weather data, such as a pattern of multiple days of rain in a row, and so forth.

In one example, the stressors may be extracted from the user data, where the extracted stressors may be input to the stress prediction model. In another example, the stress prediction model may take the user data as input(s), where the model itself may learn the significance of the stressors that may be present in the user data (e.g., without a model creator, or an owner/operator of server(s) 116 needing to be aware of or pointing out specific stressors).

It should be noted that additional types of data may also comprise input factors to the stress prediction model. For instance, audio data from one or more devices of user 190 and/or one or more vehicles transporting user 190 (such as microphone 143 of ambulance 111) may continue to be scanned for detecting lightheartedness of user 190, or conversely somberness of user 190, or the like. For instance, if user 190 is detected to be using specific words, phrases, or profession-specific terms/codes that are considered to be jokes, an input factor quantifying lightheartedness may be included in an input vector to the stress prediction model, which may tend to cause the output of the stress prediction model to lean towards a stress score that is not indicative of excessive stress.

To further illustrate, server(s) 116 may first determine that user 190 has experienced a trauma event in accordance with one or more classification/detection models for one or more defined trauma event types (based on visual and/or audio data from mobile device 115, AR device 112, camera 141, microphone 143, etc.). Server(s) 116 may then apply additional data relating to user 190 to a stress prediction model to obtain an output stress score/prediction. If the stress score is not indicative of excessive stress (e.g., the stress score is below a threshold stress score on an applicable scale, such as a perceived stress scale (PSS)), server(s) 116 may continue to monitor user 190 by gathering additional data to DB(s) 118 and applying an updated data set/input vector to the stress prediction model (e.g., twice daily for one month, or the like). In one example, if the output of the stress prediction model at any time is a stress score indicative of excessive stress (e.g., the stress score is over the threshold), server(s) 116 may then generate an alert/warning for user 190. For instance, the alert may be transmitted to mobile device 115 and/or one or more other devices of user 190. For example, a traumatic stress monitoring app on the mobile device 115 may receive the alert and present the alert on the mobile device 115 for the user 190. The presentation of the alert may be in audio form, visual form, or both. For instance, the user may be presented with a notification on a lock screen, or the app may automatically open a window to present a warning on the screen the next time the user 190 unlocks the mobile device 115. The warning may simply present the stress score, may indicate "excess stress detected," or may present one or more predefined suggested actions to the user 190, such as "please make an appointment with the wellness staff."

In one example, mobile device 115 and/or other devices of user 190 may take additional defined automated actions in response to a detection of excess stress, which may be pre-authorized by the user, such as limiting screen time, limiting in-app purchases, and so forth. Alternatively, or in addition, server(s) 116 may also transmit the alert to one or more authorized additional recipients. For instance, the alert may be sent to a spouse or other family members of a user, an authorized person or department of an organization employing the user 190 (e.g., a social worker, a staff psychologist, or psychiatrist of a police department, a fire department, EMS unit, etc.), or the like, such as via device 114.

It should be noted that the foregoing are just several examples of determining a stress score in response to detecting a trauma event of a defined trauma event type in at least one of visual data or audio data via at least one classification model, and that other, further, and different examples may be established in connection with the example of FIG. 1. It should also be noted that any number of server(s) 116 or database(s) 118 may be deployed. In one example, network 102 may also include an application server (AS) 104 and a database (DB) 106. In one example, AS 104 may perform the same or similar functions as server(s) 116. Similarly, DB 106 may store the same or similar information as DB(s) 118. For instance, network 102 may provide a traumatic stress monitoring service to subscribing users and/or devices, e.g., in addition to television, phone, and/or other telecommunication services. In one example, the traumatic stress monitoring service may reside within dedicated slice 107 and may be provided to types/categories of users having endpoint devices that are provided network services via dedicated slice 107 (e.g., first responders, governmental entities, etc.).

In one example, AS 104, DB 106, server(s) 116, and/or DB(s) 118, or any one or more of such devices in conjunction with one or more of: mobile device 115, camera 141, microphone 143, AR device 112, biometric device 113, and so forth, may operate in a distributed and/or coordinated manner to perform various steps, functions, and/or operations described herein. Similarly, in one example, steps, functions, and/or operations of server(s) 116 described above may alternatively or additionally be performed on a user device, such as mobile device 115. For instance, mobile device 115 may store user data of user 190, such as described above. In one example, server(s) 116 may detect a traumatic event and may notify mobile device 115. Mobile device 115 may then apply a stress detection model to determine whether the user 190 is experiencing excessive stress (or to determine that it is predicted that the user will suffer from excessive stress in the near future). In addition, mobile device 115 may generate an alert (if indicated by the output of the stress detection model) locally at mobile device 115. In this way, user data may be stored in the custody of user 190, while server(s) 116 may have a more limited role in identifying trauma events (e.g., scanning visual and/or audio data in real-time (e.g., as soon as practicable, and without storing any such visual or audio data other than as necessary to make a determination of whether a traumatic event is found in the content or not)). In still another example, the trauma event detection (e.g., the application of trauma event detection/classification model(s)) may also be provided by mobile device 115.

In addition, it should be noted that the system 100 has been simplified. Thus, the system 100 may be implemented in a different form than that which is illustrated in FIG. 1, or may be expanded by including additional endpoint devices, access networks, network elements, application servers, etc. without altering the scope of the present disclosure. In addition, system 100 may be altered to omit various elements, substitute elements for devices that perform the same or similar functions, combine elements that are illustrated as separate devices, and/or implement network elements as functions that are spread across several devices that operate collectively as the respective network elements. For example, the system 100 may include other network elements (not shown) such as border elements, routers, switches, policy servers, security devices, gateways, a content distribution network (CDN) and the like. Similarly, although only two access networks 120 and 122 are shown, in other examples, access networks 120 and/or 122 may each comprise a plurality of different access networks that may interface with network 102 independently or in a chained manner. For example, device 114 and server(s) 116 may be in communication with network 102 via different access networks, mobile device 115, AR device 112, biometric device 113, camera 141, and microphone 143, may be in communication with network 102 via two or more different access networks, and so forth. Thus, these and other modifications are all contemplated within the scope of the present disclosure.

Figure 2:
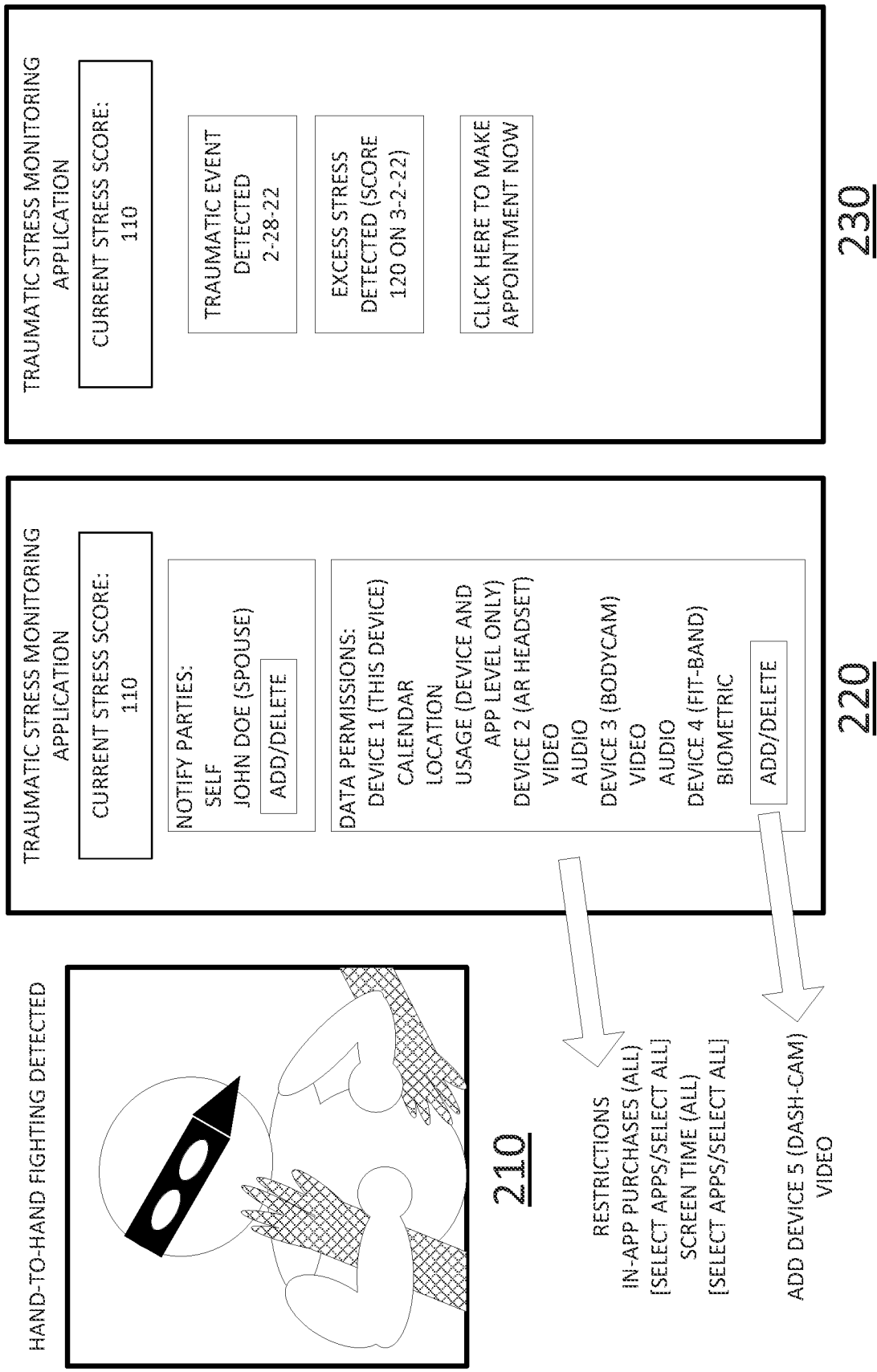
FIG. 2 illustrates an example of visual data from which a traumatic event may be detected and example screens of a user interface of a traumatic stress monitoring service, in accordance with the present disclosure.

To further aid in understanding the present disclosure, FIG. 2 illustrates an example of visual data from which a traumatic event may be detected and example screens of a user interface of a traumatic stress monitoring service, in accordance with the present disclosure. For instance, FIG. 2 illustrates an image 210, which may be a still image or a frame from a video captured via an AR device of a user (who, for illustrative purposes, may be a police officer). The image 210 appears to depict the user struggling in a hand-to-hand altercation with another person. Accordingly, the image 210 may be applied by a device of the user, by a network-based server, or other processing systems as an input to one or more classification/detection models for one or more different types of trauma events. In this example, it may be assumed that a trauma event detection model for "hand-to-hand fighting" may generate an output indicating that such hand-to-hand fighting is detected in the image 210.

FIG. 2 further illustrates example screens 220 and 230, which may be presented via a website or app for a traumatic stress monitoring service. In a first example screen 220, a first portion of the screen 220 may present a current stress score of a user, which may be "110" (for instance the scale may be zero to 150, indicating that the user's stress score (e.g., as automatically determined via a stress prediction model) may be elevated, but not excessive). A second portion of the screen 220 may list authorized "notify parties;" those who may be provided alerts when a user has an excessive stress score following a detected traumatic event. In this case, the authorized notify parties are the user (self) and John Doe (the user's spouse). The second portion of the screen 220 may further include an "add/delete" button, which may be selected by the user to add or delete authorized notify parties.

As further illustrated in FIG. 2, the example screen 220 may include a third portion that includes "data permissions;" devices from which the traumatic stress monitoring service is authorized to obtain user data, and the types of data that the traumatic stress monitoring service may obtain from such devices. In this case, the user has authorized various data to be collected from four devices: the device presenting the screen 220 (e.g., a mobile smartphone or the like), an AR headset, a body-worn camera (bodycam), and a fitness band (fit-band). The third portion of the screen 220 may also include an "add/delete" button, which may be selected by the user to add or delete devices, and/or data-collecting permission(s) associated with such devices. For instance, the user may add a fifth authorized device, such as a dashboard-mounted camera of a vehicle (dash-cam), and may authorize the collection/use of visual data (e.g., video) from the dash-cam.

It should be noted that the example screen 220 is just one example of how a screen for a traumatic stress monitoring service may be arranged, and that in other, further, and different examples, more or less information may be presented on a single screen, the information may be presented in a different form, and so forth. For instance, in one example, a main screen (not shown) may include selectable buttons or other user interface elements to allow the user to access additional, separate screens for notify parties and data permissions, respectively. Alternatively, or in addition, screen 220 and/or a different screen may include a portion for "restrictions;" e.g., automated actions that may be implemented on the device and/or other devices associated with the user in response to a detection of excessive stress following a detected trauma event of a defined trauma event type. For instance, the user may preconfigure the device presenting screen 220 to restrict all in-app purchases, in-app purchases for selected apps, or the like. Similarly, the user may restrict screen time, such as setting daily limits for all apps or selected apps. In one example, restrictions may be set for other devices associated with the user, such a home computer, television, etc.

A second example screen 230 illustrates one example of what may be presented to a user following a determination of excess stress after a detection of a trauma event of a defined trauma event type. For example, a first portion of the screen 230 may include a current stress score (e.g., "110"). A second portion of the screen 230 may include a date that the trauma event was detected. In one example, the type of trauma event is not listed, to avoid inadvertently causing more stress to the user. However, in another example, the type of trauma event may be listed along with the date. A third portion of the screen 230 may indicate the highest stress score detected and the date on which it was detected, e.g., "120" on Mar. 2, 2022. It should be noted that the current stress score of "110" may be different from the highest detected stress score. For instance, the user may ignore an initial alert and may continue to be presented with screen 230 each time the user turns on the device, each time the user accesses the traumatic stress monitoring app, periodically throughout a day until the alert is acknowledged, etc.

In this regard, the example screen 230 includes a fourth portion, which may contain a selectable button or other user interface elements that may be selected by the user to make an appointment, e.g., to see a specialist, such as a police department psychologist, or the like. For instance, recommending a session with a specialist may be a configured default response to excess stress following a detected trauma event. Other selectable options may include notifying others (who may not be on the notify party list of screen 220), requesting time off, and so forth. Thus, these and other modification are all contemplated within the scope of the present disclosure.

Figure 3:
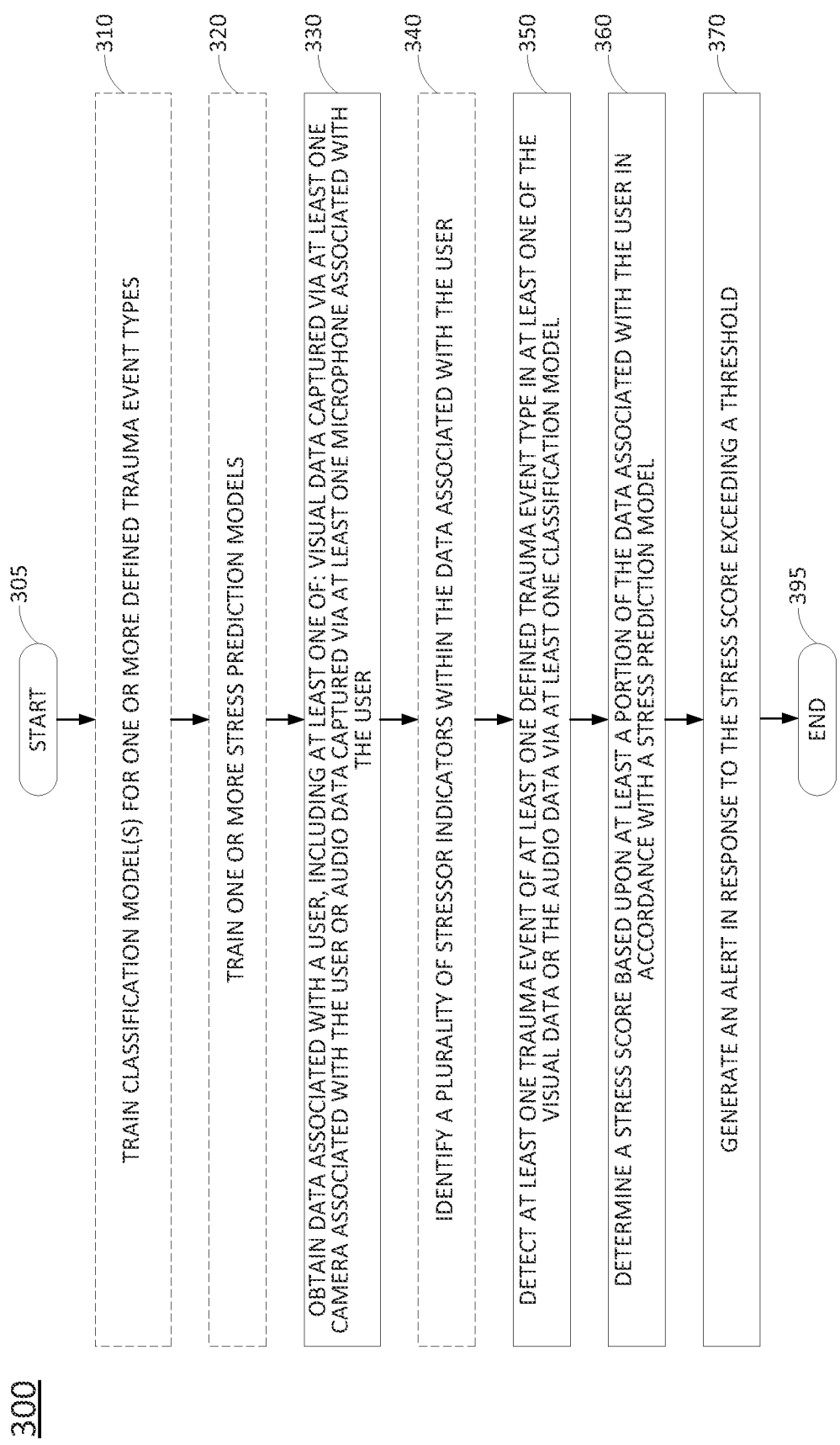
FIG. 3 illustrates a flowchart of an example method for determining a stress score in response to detecting a trauma event of a defined trauma event type in at least one of visual data or audio data via at least one classification model.

FIG. 3 illustrates a flowchart of an example method 300 for determining a stress score in response to detecting a trauma event of a defined trauma event type in at least one of visual data or audio data via at least one classification model. In one example, the method 300 is performed by a network-based component of the system 100 of FIG. 1, such as by server(s) 116, application server 104, and/or any one or more components thereof (e.g., a processor, or processors, performing operations stored in and loaded from a memory), by server(s) 116 and/or application server 104 in conjunction with one or more other devices, such as DB 106, DB(s) 118, mobile device 115, AR device 112, biometric device 113, camera 141, microphone 143, ambulance 111, and so forth. In another example, the method 300 may be performed by an endpoint device, such as mobile device 115 or AR device 112 of FIG. 1, or the like. In one example, the steps, functions, or operations of method 300 may be performed by a computing device or system 400, and/or processor 402 as described in connection with FIG. 4 below. For instance, the computing device or system 400 may represent any one or more components of a device, server, and/or application server in FIG. 1 that is/are configured to perform the steps, functions and/or operations of the method 300. Similarly, in one example, the steps, functions, or operations of method 300 may be performed by a processing system comprising one or more computing devices collectively configured to perform various steps, functions, and/or operations of the method 300. For instance, multiple instances of the computing device or processing system 400 may collectively function as a processing system. For illustrative purposes, the method 300 is described in greater detail below in connection with an example performed by a processing system. The method 300 begins in step 305 and may proceed to optional step 310, optional step 320, or step 330.

At optional step 310, the processing system (e.g., at least one server and/or an endpoint device of the user) may train classification/detection model(s) (e.g., MLMs) for one or more defined trauma event types. In one example, the defined trauma event type(s), and hence the associated classification model(s), may be profession-specific (e.g., different models may be trained for different types of first responders or others). Each classification model may be trained with training data comprising samples of video or still images that may be labeled as exhibiting a trauma event of a same trauma event type. In one example, negative examples may also be labeled and provided. Alternatively, or in addition, one or more classification models may be trained with training data comprising audio samples that may be labeled as exhibiting a trauma event of a same trauma event type (e.g., "discharged firearm," "human in severe pain," etc.).

At optional step 320, the processing system may train one or more stress prediction models (e.g., MLMs, regression models, or the like). For instance, in one example, different stress prediction models may be trained for different types/categories of users. In another example, a stress prediction model may be trained and deployed for all users, or multiple types/categories of users. As noted above, a stress prediction model may take a plurality of stressor indicators as inputs (or various user data containing latent stressor indicators), and may output a stress score. Thus, for a given stress prediction model, optional step 320 may comprise training the stress prediction model with a plurality of training data samples, e.g., data sets/input vectors comprising sets of the above data points of a plurality of users having quantified/known stress scores (and having user data including various stressor indicators). In other words, the training data may comprise labeled samples (e.g., labeled with the known stress scores, such as in accordance with a perceived stress scale (PSS)). The training data samples may include calendar data, device usage data (e.g., total screen time, per app usage, amount of in-app purchasing, etc.), device location data, biometric data, environment data, and/or other types of data as noted above (and which may include stressor indicators that may be used for predicting a stress score). Alternatively, or in addition, the training data samples may include stressor indicators extracted from such user data.

In one example, the stress prediction model may comprise a DNN, such as a CNN, a GBDT, a SVM or other MLMs such as described above (e.g., a trained MLA). In one example, the stress prediction model may comprise a regression model. Accordingly, in one example, optional step 320 may comprise performing a regression analysis to learn a relation between calendar data, device usage data, device location data, biometric data, environment data, and/or other types of data as noted above (e.g., values of such data) or stressor indicators (e.g., values thereof) extracted from such user data as predictors, and stress scores as outcomes. In one example, the regression analysis may be a multiple regression analysis (MRA). In one example, the result of regression is a prediction model (e.g., a MLM) for predicting a stress score of a user based upon at least a portion of available user data associated with the user (or stressor indicators extracted therefrom).

At step 330, the processing system obtains data associated with a user, wherein the data associated with the user includes at least one of: visual data captured via at least one camera associated with the user or audio data captured via at least one microphone associated with the user. For instance, the user may have previously enrolled and granted permission for visual and/or audio data to be collected and used for trauma event detection in accordance with the present disclosure. The at least one camera may comprise, for example, a body-worn camera, such as a chest-mounted bodycam, an AR headset, a helmet-mounted camera, or the like. Alternatively, or in addition, the at least one camera may comprise a camera of a vehicle operated by the user or in which the user is a passenger, such as a dash-cam, a camera capturing images and/or video of an interior of a vehicle, e.g., a camera in the rear of an ambulance, a camera within the cab of a fire truck or fire engine, etc. Similarly, the at least one microphone may be contained with a device carried by or worn by the user, or may be installed in a vehicle in which the user is being transported (as a driver or passenger). The data associated with the user may further be obtained from user devices, sensor device, or the like, and may include calendar data, device usage data, device location data (e.g., location data of the user), biometric data, environment data, and/or other types of data as noted above (and which may include stressor indicators that may be used for predicting a stress score in subsequent steps). For instance, the data may include a quantity of time at work for the user within a first designated time period, a commute time of the user within a second designated time period, at least one personal event of the user, an amount of time on screen for the user within a third designated time period, and so forth. It should be noted that in one example, the designated time periods may be the same, while in another example the designated time periods may be different. For example, different retention periods may be applied for different types of user data. In one example, the user may be of a designated category of one of: a first responder, a medical professional, a military professional, or a professional vehicle operator.

At optional step 340, the processing system may identify a plurality of stressor indicators within the data associated with the user. For instance, optional step 340 may include a formulaic scanning of the user data to identify defined stressor indicators, such as unusually high screen usage (e.g., daily screen usage more than 3 times the average daily screen usage of the user over the last 30 days), screen usage in excess of an absolute threshold (e.g., more than X minutes per day)), insufficient sleep (e.g., quantified as less than an absolute threshold for more than X days in a row (e.g., less than 6 hours per day for at least 5 days, less than 5 hours per day for at least 3 days, etc.)), excess sleep (e.g., quantified as more than 11 hours of sleep for more than four days within a past 7 day period), excessive commute time (e.g., more than 2 hour each way per day for 4 or more days, or more than 50 percent longer weekly commuting time as compared to a weekly average over the past two months for the user, or the like), stops at designated landmarks (e.g., casino, bar, liquor store, etc.), elevated heart rate (e.g., resting heart rate 20 percent or more over an average resting heart rate of the user over the past two months, or the like), and so forth.

At step 350, the processing system detects at least one trauma event of at least one defined trauma event type in at least one of: the visual data or the audio data via at least one classification model. For instance, the at least one classification model may be trained at optional step 310 as described above. The visual data and/or the audio data may be obtained at step 330. In one example, step 350 may include applying the visual data and/or the audio data as input(s) to the at least one classification model, wherein an output of the at least one classification model is an indication of a trauma event of the associated defined trauma event type being detected (or in another example, no trauma event of the associated defined trauma event type being detected). In one example, the at least one defined trauma event type is one of a plurality of defined trauma event types (e.g., each having a respective classification model). As such, the at least one classification model may be trained to detect trauma events of the at least one defined trauma event type. In one example, the at least the portion of the data associated with the user may be from at least one designated time period in relation to the at least one trauma event (e.g., one of the first, second, and/or third designated time periods such as mentioned above). In this regard, it should be noted that the at least one designated time period may precede the at least one trauma event, include the at least one trauma event, and/or follow the at least one trauma event.

At step 360, the processing system determines a stress score based upon at least a portion of the data associated with the user in accordance with a stress prediction model. For instance, at least a portion of the data associated with the user may be used as inputs, e.g., an input vector, to the stress prediction model. In one example, step 360 may comprise determining the stress score based upon the plurality of stressor indicators that may be identified at optional step 340 in accordance with the stress prediction model. For instance, the plurality of stressor indicators may comprise an input vector to the stress prediction model, which may output the stress score. In other words, in one example, the stress prediction model may be trained to learn latent stressor indicators in user data upon which the stress score may be predicted. However, in another example, the user data is scanned for specific stressor indicators that are predefined (e.g., by a system operator), upon which the stress prediction model is then trained and deployed for making stress score predictions. It should also be noted that in still another example, the stress prediction model may comprise a formula-based model that weights the plurality of stressor indicators. For example, the formula based model may add or subtract from a stress score in accordance with various rules, such as +2 for double normal screen time, +4 for triple normal screen time, +7 for work in excess of 70 hours, −5 for vacation within the last month, −2 for each exercise session within the last 7 days, −1 for a stop in a bar, +1 if the stop in the bar was a scheduled stop to meet a friend or family member, etc.

At step 370, the processing system generates an alert in response to the stress score exceeding a threshold. In one example, the threshold may be a set value on a perceived stress scale (PSS), such as any stress score greater than or equal to 120 on a scale of 150, any stress score greater than 9 on a scale of 0 to 10, etc. In one example, the threshold may be specific to a type or category of the user (e.g., different thresholds may be used for different user types/categories, such as a first threshold for firefighters, a second threshold for EMS users, etc.). In one example, the threshold may be ratio-based, e.g., depending upon the amount of user data that may be collected. For example, different users may have authorized the processing system to access different types of user data and/or authorized the retention of user data for different amounts of time. Thus, for a formula-based stress score, if a user's sleep data is not available, the threshold may be adjusted to account for the fact that this data is not contributing to the score (e.g., the threshold may be lowered since even if the user is suffering from poor sleep, this data is not available to contribute to a higher stress score).

In one example, step 370 may comprise transmitting the alert to the user (e.g., wherein the processing system is a network-based processing system) and/or to one or more other authorized recipients. In one example, the alert may be presented on a user device, such as illustrated in screen 230 of FIG. 2. In one example, step 370 may further include applying one or more automated actions in response to the alert, such as applying screen time restrictions, in-app purchase restrictions, or the like on one or more user devices, presenting a recommendation to the user, such as a recommendation to take time off of work, to make an appointment with staff psychologist or the like, providing a link to assist the user in making such an appointment, and so forth.

Following step 370, the method 300 proceeds to step 395 where the method ends.

It should be noted that the method 300 may be expanded to include additional steps, or may be modified to replace steps with different steps, to combine steps, to omit steps, to perform steps in a different order, and so forth. For instance, in one example, the processing system may repeat some or all of steps 330-370, e.g., on an ongoing basis after detecting at least one trauma event until an excessive stress score is determined or until a designated amount of time has passed since the detection of the trauma event, such as after 60 days, 90 days, etc. In one example, the method 300 may further include obtaining user permission(s) for the collection of user data from one or more devices of the user, the types of user data for which such permission(s) are granted, the durations over which such users data may be collected and/or retained, and so forth. Similarly, in one example, the method 300 may further include obtaining user permission(s) for one or more notify parties (e.g., recipients of alerts that may be generated in accordance with step 370), obtaining user permissions/authorization for automated actions to take in connection with step 370 (such as in-app purchase restrictions, etc.), and so forth. In one example, the user data from which stressor indicators may be extracted and/or via which a stress score may be predicted may further comprise additional visual and/or audio data. For instance, the stress prediction model may account for the detection of additional trauma events as additional input factors/predictors. To illustrate, the resulting stress score may be higher when there are multiple trauma events detected within the relevant time period(s) before, contemporaneous with, or after the trauma event detected at step 350. In one example, the method 300 may be expanded or modified to include steps, functions, and/or operations, or other features described above in connection with the example(s) of FIGS. 1 and 2, or as described elsewhere herein. Thus, these and other modifications are all contemplated within the scope of the present disclosure.

In addition, although not expressly specified above, one or more steps of the method 300 may include a storing, displaying and/or outputting step as required for a particular application. In other words, any data, records, fields, and/or intermediate results discussed in the method can be stored, displayed and/or outputted to another device as required for a particular application. Furthermore, operations, steps, or blocks in FIG. 3 that recite a determining operation or involve a decision do not necessarily require that both branches of the determining operation be practiced. In other words, one of the branches of the determining operation can be deemed as an optional step. Furthermore, operations, steps or blocks of the above described method(s) can be combined, separated, and/or performed in a different order from that described above, without departing from the example embodiments of the present disclosure.

FIG. 4 depicts a high-level block diagram of a computing device or processing system specifically programmed to perform the functions described herein. For example, any one or more components or devices illustrated in FIG. 1 or described in connection with the examples of FIG. 2 or 3 may be implemented as the processing system 400. As depicted in FIG. 4, the processing system 400 comprises one or more hardware processor elements 402 (e.g., a microprocessor, a central processing unit (CPU) and the like), a memory 404, (e.g., random access memory (RAM), read only memory (ROM), a disk drive, an optical drive, a magnetic drive, and/or a Universal Serial Bus (USB) drive), a module 405 for determining a stress score in response to detecting a trauma event of a defined trauma event type in at least one of visual data or audio data via at least one classification model, and various input/output devices 406, e.g., a camera, a video camera, storage devices, including but not limited to, a tape drive, a floppy drive, a hard disk drive or a compact disk drive, a receiver, a transmitter, a speaker, a display, a speech synthesizer, an output port, and a user input device (such as a keyboard, a keypad, a mouse, and the like).

Although only one processor element is shown, it should be noted that the computing device may employ a plurality of processor elements. Furthermore, although only one computing device is shown in the Figure, if the method(s) as discussed above is implemented in a distributed or parallel manner for a particular illustrative example, i.e., the steps of the above method(s) or the entire method(s) are implemented across multiple or parallel computing devices, e.g., a processing system, then the computing device of this Figure is intended to represent each of those multiple general-purpose computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented. The hardware processor 402 can also be configured or programmed to cause other devices to perform one or more operations as discussed above. In other words, the hardware processor 402 may serve the function of a central controller directing other devices to perform the one or more operations as discussed above.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computing device, or any other hardware equivalents, e.g., computer readable instructions pertaining to the method(s) discussed above can be used to configure a hardware processor to perform the steps, functions and/or operations of the above disclosed method(s). In one example, instructions and data for the present module or process 405 for determining a stress score in response to detecting a trauma event of a defined trauma event type in at least one of visual data or audio data via at least one classification model (e.g., a software program comprising computer-executable instructions) can be loaded into memory 404 and executed by hardware processor element 402 to implement the steps, functions or operations as discussed above in connection with the example method(s). Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for determining a stress score in response to detecting a trauma event of a defined trauma event type in at least one of visual data or audio data via at least one classification model (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not limitation. Thus, the breadth and scope of a preferred embodiment should not be limited by any of the above-described example embodiments, but should be defined only in accordance with the following claims and their equivalents.

What is claimed is:

1. A method comprising:
   obtaining, by a processing system including at least one processor, data associated with a user, wherein the data associated with the user includes at least one of: visual data captured via at least one camera associated with the user or audio data captured via at least one microphone associated with the user, wherein the data associated with the user further comprises calendar data of the user, and wherein the calendar data includes at least one of: a quantity of time at work for the user within a designated time period or a commute time of the user within the designated time period;
   detecting, by the processing system, at least one trauma event of at least one defined trauma event type in at least one of: the visual data or the audio data via at least one classification model;
   identifying, by the processing system, a plurality of stressor indicators within the data associated with the user including at least the calendar data of the user;
   determining, by the processing system responsive to the detecting of the at least one trauma event, a stress score of the user based upon at least a portion of the data associated with the user in accordance with a stress prediction model, wherein the determining the stress score of the user comprises determining the stress score of the user based upon the plurality of stressor indicators in accordance with the stress prediction model; and
   generating, by the processing system, an alert in response to the stress score of the user exceeding a threshold.

2. The method of claim 1, wherein the at least one defined trauma event type is one of a plurality of defined trauma event types.

3. The method of claim 1, wherein the at least one classification model is trained to detect trauma events of the at least one defined trauma event type.

4. The method of claim 1, wherein the data associated with the user further comprises at least one of:
   location data of the user;
   environmental data of an environment of the user; or
   biometric data of the user.

5. The method of claim 1, wherein the calendar data further includes at least one of:
   at least one personal event of the user.

6. The method of claim 1, wherein the data associated with the user further comprises a quantity of time on screen for the user within a designated time period.

7. The method of claim 1, wherein the user is of a designated category of one of:
- a first responder;
- a medical professional; or
- a professional vehicle operator.

8. The method of claim 1, wherein the at least the portion of the data associated with the user is from at least one designated time period in relation to the at least one trauma event.

9. The method of claim 8, wherein the at least one designated time period in relation to the at least one trauma event precedes the at least one trauma event, includes the at least one trauma event, or follows the at least one trauma event.

10. The method of claim 1, wherein the stress prediction model comprises a machine learning model trained on a plurality of sets of data associated with a plurality of users.

11. The method of claim 10, wherein each of the plurality of sets of data is labeled with one of:
- a respective stress score; or
- a respective label of excess stress or non-excess stress.

12. The method of claim 1, wherein the stress prediction model comprises a regression model.

13. The method of claim 1, wherein the stress prediction model comprises a formula-based model that weights the plurality of stressor indicators.

14. The method of claim 1, wherein the at least one camera associated with the user comprises at least one of:
- a body-worn camera; or
- a camera of a vehicle operated by the user or in which the user is a passenger.

15. The method of claim 1, wherein the processing system comprises at least one server, or an endpoint device of the user.

16. The method of claim 1, wherein the alert is provided to at least one of:
- the user via an endpoint device of the user; or
- a designated authorized entity.

17. A non-transitory computer-readable medium storing instructions which, when executed by a processing system including at least one processor, cause the processing system to perform operations, the operations comprising:
- obtaining data associated with a user, wherein the data associated with the user includes at least one of: visual data captured via at least one camera associated with the user or audio data captured via at least one microphone associated with the user, wherein the data associated with the user further comprises calendar data of the user, and wherein the calendar data includes at least one of: a quantity of time at work for the user within a designated time period or a commute time of the user within the designated time period;
- detecting at least one trauma event of at least one defined trauma event type in at least one of the visual data or the audio data via at least one classification model;
- identifying a plurality of stressor indicators within the data associated with the user including at least the calendar data of the user;
- determining, responsive to the detecting of the at least one trauma event, a stress score of the user based upon at least a portion of the data associated with the user in accordance with a stress prediction model, wherein the determining the stress score of the user comprises determining the stress score of the user based upon the plurality of stressor indicators in accordance with the stress prediction model; and
- generating an alert in response to the stress score of the user exceeding a threshold.

18. An apparatus comprising:
a processing system including at least one processor; and
a computer-readable medium storing instructions which, when executed by the processing system, cause the processing system to perform operations, the operations comprising:
- obtaining data associated with a user, wherein the data associated with the user includes at least one of: visual data captured via at least one camera associated with the user or audio data captured via at least one microphone associated with the user, wherein the data associated with the user further comprises calendar data of the user, and wherein the calendar data includes at least one of: a quantity of time at work for the user within a designated time period or a commute time of the user within the designated time period;
- detecting at least one trauma event of at least one defined trauma event type in at least one of the visual data or the audio data via at least one classification model;
- identifying a plurality of stressor indicators within the data associated with the user including at least the calendar data of the user;
- determining, responsive to the detecting of the at least one trauma event, a stress score of the user based upon at least a portion of the data associated with the user in accordance with a stress prediction model, wherein the determining the stress score of the user comprises determining the stress score of the user based upon the plurality of stressor indicators in accordance with the stress prediction model; and
- generating an alert in response to the stress score of the user exceeding a threshold.

19. The apparatus of claim 18, wherein the at least one defined trauma event type is one of a plurality of defined trauma event types.

20. The apparatus of claim 18, wherein the at least one classification model is trained to detect trauma events of the at least one defined trauma event type.

\* \* \* \* \*